United States Patent [19]

Nohda et al.

[11] 4,353,625

[45] Oct. 12, 1982

[54] EYE-REFRACTOMETER DEVICE

[75] Inventors: Masao Nohda, Yokohama; Izumi Umemura, Kawasaki, both of Japan

[73] Assignee: Nippon Kogaku K.K., Tokyo, Japan

[21] Appl. No.: 152,602

[22] Filed: May 23, 1980

[30] Foreign Application Priority Data

Jun. 2, 1979 [JP] Japan ................................ 54-69083

[51] Int. Cl.³ ........................... A61B 3/14; A61B 3/10
[52] U.S. Cl. ...................................... 351/13; 351/14; 351/7
[58] Field of Search .......................... 351/7, 13, 14, 6; 250/200

[56] References Cited

U.S. PATENT DOCUMENTS 3,136,839  6/1964  Safir .
3,715,166  2/1973  Leighty et al. .
4,173,398  11/1979  Okamoto ........................ 351/13 X Primary Examiner—John K. Corbin
Assistant Examiner—Rodney Bovernick
Attorney, Agent, or Firm—Fitzpatrick, Cella, Harper & Scinto

[57] ABSTRACT

An eye-refractometer device includes a light receiving member having a pair of photoelectric elements for detection of astigmatic axis and a pair of photoelectric elements for detection of diopter of an eye provided on the light receiving surface of said member off the optical axis of a condenser lens. Said pair of astigmatic axis detection photoelectric elements are positioned on a straight line normal to the scanning direction of the beam projected through said projection optical system. Said pair of diopter detection photoelectric elements are positioned on a line extending in said scanning direction. The eye-refractometer device has a highly improved accuracy of measurement of diopter.

8 Claims, 22 Drawing Figures

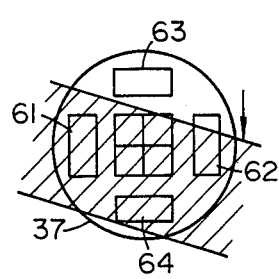
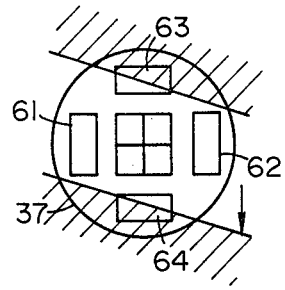
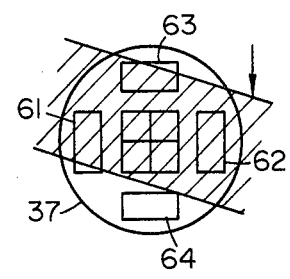
FIG. 6A    FIG. 6B    FIG. 6C
SIGNAL OF 61
FIG. 7A
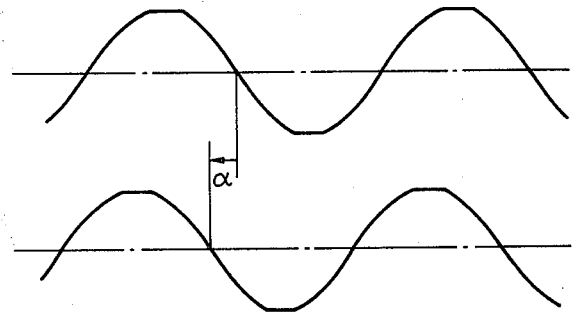
SIGNAL OF 62
FIG. 7B
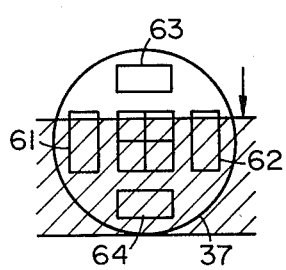
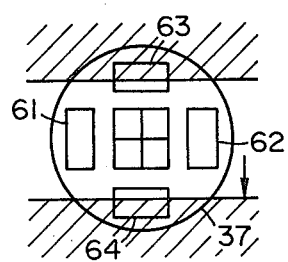
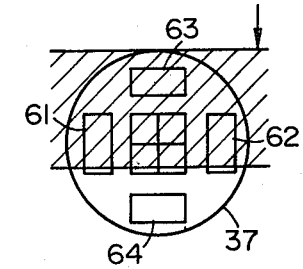
FIG. 8A    FIG. 8B    FIG. 8C

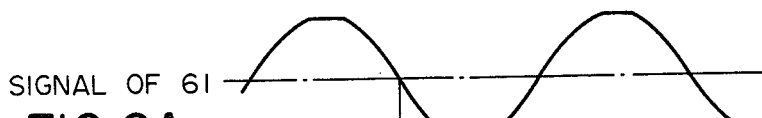
FIG. 9A SIGNAL OF 61
FIG. 9B SIGNAL OF 62
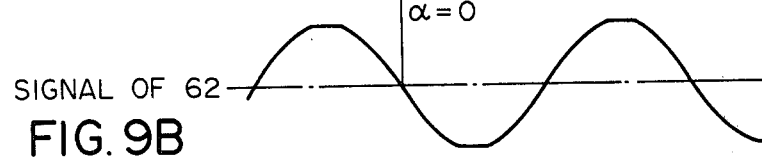
FIG. 10
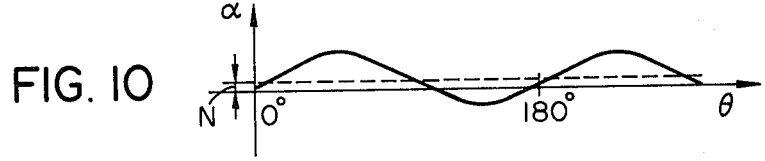
FIG. 11A SIGNAL OF 63
FIG. 11B SIGNAL OF 64
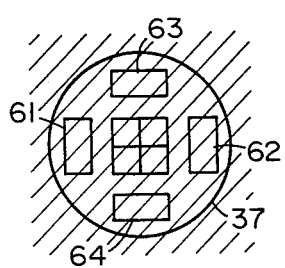
FIG. 12A
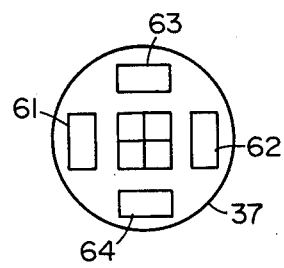
FIG. 12B
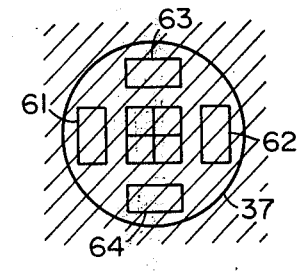
FIG. 12C

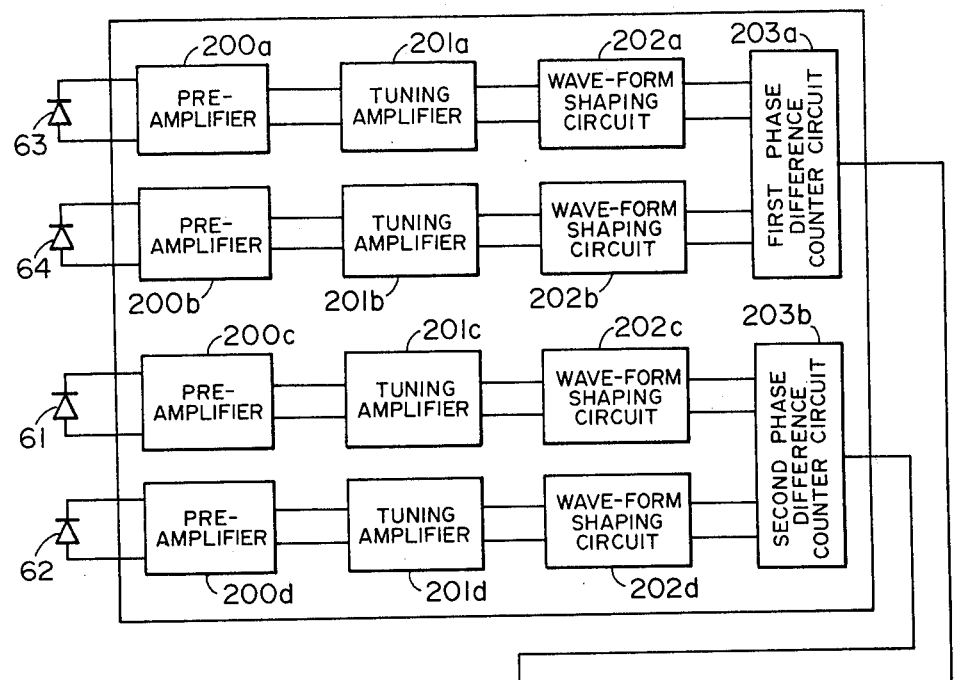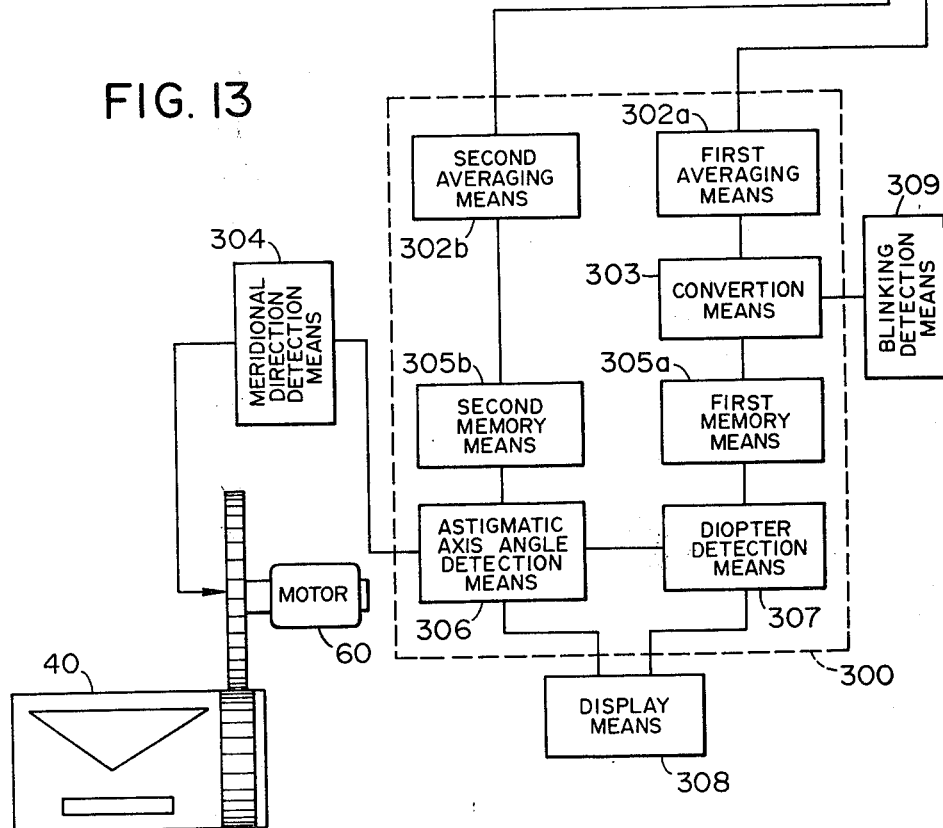
FIG. 13

EYE-REFRACTOMETER DEVICE

BACKGROUND OF THE INVENTION

1. Field of the Invention

This invention relates to improvements over an eye-refractometer device using retinoscopy.

2. Description of the Prior Art

Generally, in the measurement of diopter of an eye, it is necessary to first detect the direction of the astigmatic principal meridians, and then measure the diopter in that direction. A device for carrying out such measurement by the use of retinoscopy is already known. Retinoscopy is such that a slit-like light is sent into the pupil of the eye to be examined and when that light is moved, the movement exhibited in the pupil by the reflected light from the retina of the eye is observed, whereby the neutralized condition in which the light becomes unmoved is found out. There are two types of such method, namely, one in which a lens having various refractive powers is disposed immediately before the eye to be examined so that the eye is observed from a predetermined position to obtain the diopter by a lens bringing about the neutralized condition, and one in which the eye is observed by varying the observation distance so that the diopter is obtained from a distance providing the neutralized condition. As the devices for photoelectrically measuring the diopter of the eye by retinoscopy, a device using the former method is disclosed in U.S. Pat. No. 3,136,839 and a device using the latter method is disclosed in U.S. Pat. No. 3,715,166. In these measuring devices, the entire device is rotated to detect the direction of the astigmatic axis of the eye to be examined and an accurate servo mechanism for making the entire device exactly coincident with the direction of the astigmatic principal meridians is indispensable. This has made the device complicated and bulky and has been prejudicial to quick measurement.

SUMMARY OF THE INVENTION

It is the object of the present invention to provide an eye-refractometer device which is simple and compact in construction and which can measure the diopter of eye accurately and quickly.

The present invention basically uses retinoscopy. and consists in an eye-refractometer device which has a projection optical system provided in one light path of a beam splitter for projecting a light beam into a pupil of an eye to be examined and scanning the light beam, a condenser optical system provided in the other light path of the beam splitter for receiving the reflected light from the retina of the eye, said condenser optical system comprising a condenser lens, a diaphragm member and a light-receiving member, and a signal processing system for processing the signal from said light-receiving member, wherein light beam rotating means for rotating the light beam about the optic axis is provided between the beam splitter and the eye, the fundus of the eye, and a signal processing system for processing the signals coming from the light-receiving member. The features of the present invention reside in that between the beam splitter and the eye there is provided beam rotating means for rotating the beam about the optical axis, two pairs of light-receiving or photoelectric elements are provided on the light-receiving surface of the light-receiving member off the optical axis, both the diaphragm member and the light-receiving member are fixedly disposed with the diaphragm member being disposed between the beam splitter and the light receiving member, and two sets of phase difference detection means are provided as the signal processing system to produce a signal of phase difference between the output signals of one pair of the above-mentioned photoelectric elements and a signal of phase difference between the output signals of another pair of the photoelectric elements respectively so that the diopter can be determined by means of the phase difference signal produced by one of said phase difference detection means and the angle of astigmatic axis can be determined by means of the phase difference signal produced by another one. With this arrangement, diopter and angle of astigmatic axis are measured independently of each other.

Other and further objects, features and advantages of the invention will appear more fully from the following description taken in connection with the accompanying drawings.

BRIEF DESCRIPTION OF THE DRAWINGS

FIGS. 6A–6C, 8A–8C and 12A–12C are plan views of the light-receiving surface to illustrate the manner how to detect the incident beam upon the surface;

FIGS. 7A and 7B, 9A and 9B, 10, and 11A and 11B show the signals derived from the lights detected by photoelectric elements arranged on the light-receiving surface; and FIG. 13 is a block diagram of the electric signal processing system used in the embodiment of the invention.

DESCRIPTION OF THE PREFERRED EMBODIMENT

Before the construction of the present invention is described, the principle of the invention will first be explained.

Figure 1:
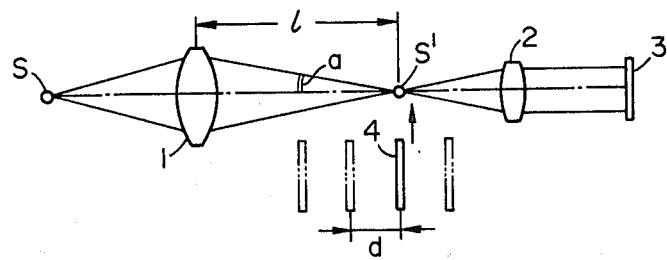
FIG. 1 shows the construction of an optical system illustrating the principle of the present invention.

Assume that, as shown in FIG. 1, the image S' of a point source of light S lying at a predetermined distance on the optic axis is formed at a distance l from a first lens 1 by the first lens 1 and that the light beam from the light source S is projected upon a light-receiving surface 3 by a second lens 2. Here, if a douser 4 lying at the distance l from the first lens 1 vertically crosses the optic axis from below to above, as viewed in FIG. 1, the light-receiving surface 3 will become dark in a moment. If the douser 4 crosses the optic axis at a distance shorter than l a shadow will run on the light-receiving surface 3 from above to below. If the douser 4 crosses the optic axis at a distance nearer to the first lens 1, a shadow will also run on the light-receiving surface 3 from above to below, but the speed of the shadow will be slower. On the other hand, if the douser 4 crosses the optic axis at a distance more remote than the light source image S', a shadow will run on the light-receiving surface 3 from below to above in contrast with the foregoing and thus, the direction of movement of the shadow will be coincident with the direction of movement of the douser 4. If the douser 4 lies at a position still more remote from the first lens 1, the speed of movement of the shadow will become slower. Thus, depending on whether the douser 4 lies forwardly or rearwardly with respect to the light source image S', the movement of the shadow on the light-receiving surface 3 differs. Therefore, assuming that the douser 4 crosses the optic axis at a predetermined position and that the refractive power of the first lens 1 is varied, the position of the light source image S' is varied in accordance with the variation in refractive power of the first lens, whereby the movement of the shadow on the light-receiving surface 3 is varied. Specifically, if the refractive power of the first lens 1 is great to such an extent that the light source image S' is formed forwardly of the douser 4, the direction of movement of the shadow on the light-receiving surface 3 will be coincident with the direction of movement of the douser 4. conversely, if the refractive power of the first lens 1 is small to such an extent that the light source image S' is formed rearwardly of the dourser 4, the shadow on the light-receiving surface 3 will move in the direction opposite to the direction of movement of the douser 4. As the relative distance between the light source image S' formed by the first lens 1 and the douser 4 is greater, the speed of movement of the shadow becomes slower. Of course, if the light source image S' is formed at the position of the douser 4, the light receiving surface will become dark in a moment.

If the time required for the shadow on the light-receiving surface 3 to run from one end to the other end is t and the distance from the douser 4 to the light source image S' is d, the following relation is established and the foregoing description is summarized in this equation.

$$t = \frac{2 \tan a}{v} \cdot d$$

where a represents the angle made by the conical light beam reaching the light source image S' with the optic axis, and v represents the speed at which the douser 4 vertically crosses the optic axis. It is seen from this equation that if the time t required for the shadow to run on the light-receiving surface is measured, d representing the position of the light source image can be obtained. The value of d corresponds to the refractive power of the first lens 1 and from this, the refractive power may immediately be obtained.

In the foregoing description, moving the douser across the optic axis is equivalent to taking out part of the light beam from the point light source in a slit form and causing that part to scan in the aperture of the first lens. If the first lens 1 is regarded as the eye to be examined, this is nothing other than the so-called retinoscopy. The present invention is thus based on the principle of measuring the speed of movement of the shadow instead of simple obtaining the neutralization point in the renitoscopy, and obtaining the diopter of the eye to be examined from this.

Figure 2:
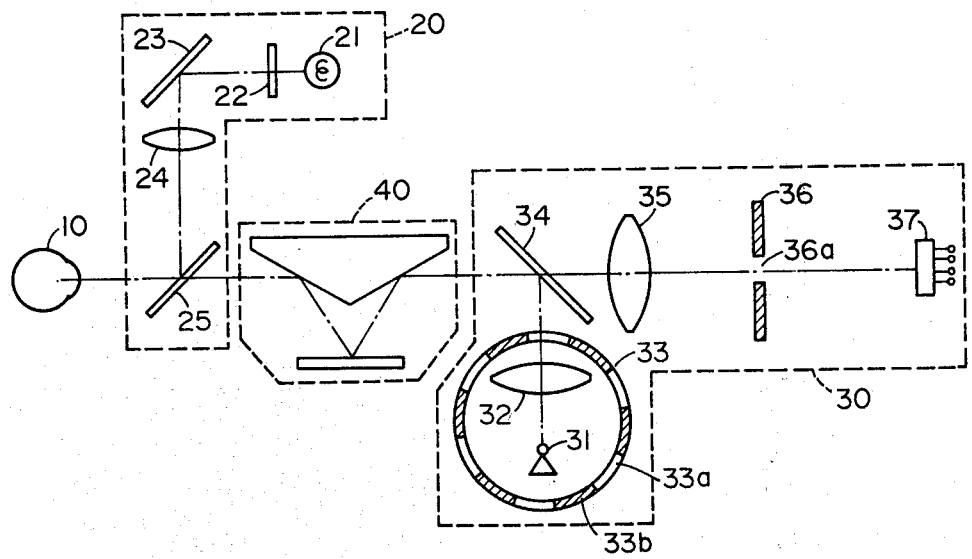
FIG. 2 shows the construction of the optical system according to an embodiment of the present invention.
Figure 3:
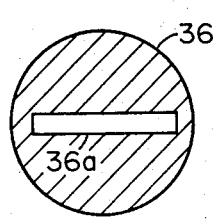
FIG. 3 shows a plan view of the structure of the diaphragm member of FIG. 2.
Figure 4:
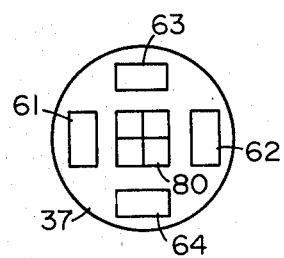
FIG. 4 shows a plan view of the construction of the light-receiving member of FIG. 2.

The construction of the present invention will hereinafter be described with respect to an embodiment thereof. FIG. 2 is a cross-sectional view schematically showing the construction of the optical system according to an embodiment of the present invention. The present embodiment generally comprises a fixation optical system 20, testing optical means 30 and light beam rotating means 40 provided between the fixation optical system 20 and the testing optical means 30. In the fixation optical system 20, a light source 21 illuminates a target 22 and the light beam from the target 22 is reflected by a mirror 23 and is substantially collimated by a collimater lens 24. This light beam is reflected by a partially reflecting mirror or beam splitter 25 and reaches the eye 10 to be examined which fixedly sees the target 22. The target 22 is movable in the direction of the optic axis and is placed each time at a position which can be fixedly seen by the eye to be examined in non-adjusted condition. The testing optical means 30 includes a projection optical system for scanning a slit-like infrared light beam in the pupil of the eye 10 to be examined and a condenser optical system for condensing the reflected light from the retina of the eye 10 to be examined. The infrared light beam from an infrared light emitting diode 31 as the light source is made into a substantially parallel light beam by a projection lens 32 and reflected by a partially reflecting mirror or beam splitter 34, and projected into the pupil of the eye 10 through light beam rotating means 40 rotatively driven intermittently in a predetermined direction by a step motor (not shown). The light-emitting diode 31 and the projection lens 32 are disposed within a rotary cylinder 33 rotatable about an axis perpendicular to the optic axis of the projection lens 32, and the light beam reaching the beam splitter 34 is chopped by a slit-like opening 33a provided in the side of the rotary cylinder 33 and becomes a slit-like light beam having a rectilinear cross-section. Accordingly, with the rotation of the rotary cylinder 33, the slit-like light beam scans the interior of the pupil of the eye 10 to be examined. Of the light beam projected into the pupil of the eye 10 to be examined, the light reflected by the retina of the eye and again passing through the beam splitter 34 via the light beam rotating means 40 is condensed by a condenser lens 35. A diaphragm member 36 as shown in FIG. 3 having a slit-like opening 36a parallel to the lengthwise direction of the projected linear (slit-like) light beam is fixedly disposed rearwardly of the condenser lens 35, and a light-receiving member 37 is fixedly disposed further rearwardly of the diaphragm member 36. The position of the light-receiving member 37 is substantially conjugate with the cornea of the eye to be examined with respect to the condenser lens 35. Accordingly, the light passed through the slit-like opening 36a reaches the light-receiving member 37 and of that light, the reflected light from the cornea of the eye to be examined is condensed at the center of the light-receiving member 37. On the surface of the light-receiving member 37 there are provided four photoelectric elements 61, 62, 63 and 64 and a four-divided photoelectric element 80 on the optical axis as shown in FIG. 4. Of the four photoelectric elements, one pair of elements 61 and 62 is almost symmetrically arranged on a straight line extending parallel with the longitudinal direction of the slit 36a. The elements 61 and 62 are substantially equally spaced from the center of the light receiving surface and constitute means for detecting astigmatic axis. Another pair of photoelectric elements 63 and 64 constitute means for detecting diopter and is almost symmetrically arranged on a straight line extending normal to the longitudinal direction of the slit 36a and at positions substantially equally spaced from the center of the light receiving surface. The photoelectric element 80 lying on the optical axis is disposed to receive the reflected light from the cornea of the eye. When the alignment of the eye with the relative to eye-refractometer device is correctly made, the reflected light from the cornea enters evenly the four divided areas in the photoelectric element 80 so that signals obtained therefrom are all equal to each other. However, if the alignment is incorrect, then irregularity will be found among the signals. Thus, the signals coming from the four divided photoelectric element 80 are useful for attaining a correct alignment.

Figure 5:
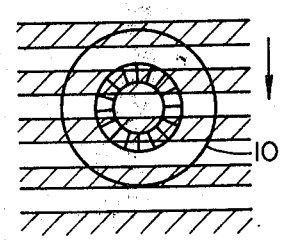
FIG. 5 is a front view of an eye to be examined being scanned by a linear beam.

FIG. 5 illustrates the manner of scanning of the eye 10 to be examined with the above described arrangement when the eye is scanned from above to below by the scanning beam having a linear cross section successively supplied to the eye from the rotary cylinder 33. In FIG. 5 which is a front view of the eye 10, the hatched area shows a shadow portion which no light reached.

If the eye 10 is astigmatic, then some difference in behaviour will be found between the beam projected on the eye and that detected by the light-receiving member 37. More specifically, for example, when the conjugate point with the fundus of the eye 10 is at a position behind the diaphragm member 36, the beam on the light receiving surface is inclined as shown in FIG. 6 and moves from above to below via the positions of FIGS. 6A, 6B and 6C in this order. Curves shown in FIGS. 7A and 7B show the forms of detection signals obtainable by the photoelectric elements 61 and 62 respectively in this case. The period of the detection signal corresponds to that of the scanning beam. The crest of the signal wave means the presence of an incident beam and the wave trough means the absence of an incident beam. As seen in FIG. 7, the signal of photoelectric element 61 has a delay time $\alpha$ relative to that of the photoelectric element 62. Magnitude and sign of this phase difference $\alpha$ correspond to shift in angle and shift in direction between the longitudinal direction of the illuminating light beam and the direction of the astigmatic principal meridians respectively. The scanning direction of the beam is rotated by the rotation of the light beam rotating means 40 about the optical axis of the condenser lens 35 by a motor for measuring the axis of astigmatism. During a rotation of the scanning direction through 180°, the inclination of the linear beam on the surface of the light-receiving member 37 usually changes continuously and takes the position shown in FIG. 8 twice. In the position shown in FIG. 8 the inclination is about to be inverted and therefore the beam incident on the light receiving surface has no inclination at this time point. The form of the beam of the surface is the same as that of the beam incident on the eye and moves from above to below as shown in FIGS. 8A, 8B and 8C in this order. This is the time when the longitudinal direction of the eye illumination light beam having a linear cross section is coincident with the direction of any one of two astigmatic principal meridians intersecting at right angle with each other. This position can be detected by reading the fact that the detection signals of the photoelectric elements 61 and 62 become coincident with each other, that is, by reading the point at which the phase difference between the two signals becomes 0 (zero) as will be seen from FIGS. 9A and 9B. Therefore, the direction of astigmatic principle meridians of the eye can be found by reading the rotational angle of beam rotating means 40 or the amount of rotation of the step motor for driving said means 40 at the time point.

However, since there are various sources of noise signal within the eye-refractometer device, it is very difficult to precisely detect the position in which the phase difference $\alpha$ between the two output signals of photoelectric elements 61 and 62 just becomes zero. Generally, this phase difference $\alpha$ varies periodically at periods of 180° for scanning angle $\theta$ of the linear beam. However, when the degree of astigmatism is small, the signal of phase difference does not detect a true zero point but detects a false angular position because of some noise bias N as shown in FIG. 10. In the worst case, no detection of the zero point is made and therefore the measurement of astigmatism becomes impossible.

To solve the above problem, according to the invention, the maximum and minimum values of phase difference between the signals of photoelectric elements 61 and 62 are used to detect the direction of astigmatic axis. In this embodiment of the invention, the extremal value of the phase difference $\alpha$ between two signals of photoelectric elements 61 and 62 corresponds to the greatest value of the inclination of the linear beam on the surface of the light-receiving member 37 and its maximum and minumim values correspond to the version of the inclination of the beam. Therefore, by obtaining the mean value of the maximum and minimum of the phase difference and reading the angle corresponding to the found mean value, the astigmatic axis can be determined. This enables accurate detection of the astigmatic axis even when the degree of astigmatism (cylindrical diopter) is very low.

Curves shown in FIGS. 11A and 11B, are an example wave forms of the detection signals as obtained by another pair of photoelectric elements 63 and 64 for detection of diopter. The period of these detection signals corresponds to the period of scanning of the above mentioned linear beam. The two signals shown in FIG. 11 appear in the position as shown in FIG. 5 or 7. Phase of the signal of photoelectric element 63 is advanced by $\beta$ relative to that of the signal of photoelectric element 64. This phase difference $\beta$ is the time required for scanning of the linear beam on the surface of the light receiving member 37. As previously described, it corresponds to the diopter at that time in the scanning direction of the linear beam projected upon the subject eye 10. Measurement of diopter in every meridian direction is made by detecting the phase difference between the output signals of photoelectric elements 63 and 64.

Here, the condenser lens 35 and the diaphragm member 36 are reverse in position but essentially similar in construction. However, in the construction shown in FIG. 2, the position of the diaphragm member 36 should desirably be coincident with the rear focus position of the condenser lens 35.

If this is done, then the eye 10 to be examined is emmetropic, the retina of the eye and the position of the diaphragm member become conjugate with each other. At this time, as shown in FIG. 12, lightening and darkening of light on the whole surface of the light-receiving member are repeated in the sequence of FIGS. 12A, 12B and 12C. Therefore, the phase difference between two photoelectric elements becomes zero at this time. This makes it possible to further simplify the signal processing system necessary for obtaining the value of diopter from the phase difference signal.

Now, description will be made of the signal processing system for obtaining the values of two refractive power, that is, spherical and cylindrical diopters, and the angle of astigmatic axis from the photoelectric signals given by the four photoelectric elements.

FIG. 13 is a block diagram of a signal processing system in an embodiment of the invention.

In the manner described above, a pair of diopter detecting photoelectric elements 63 and 64 and a pair of astigmatic axis detecting photoelements 61 and 62 receive the reflected light from the fundus of the eye to be examined. The individual elements produce photoelectric currents in an amount proportional to the quantity of light incident upon the elements, respectively. Since these photoelectric currents are weak signals, they are introduced into pre-amplifiers 200a, 200b, 200 c, 200d, respectively to obtain high level voltages signals from the weak input signals. To improve the ratio of S/N, the high level voltage signals are put into tuning amplifiers 201a, 201b, 201c, 201d, respectively. The output signals from the tuning amplifiers are of sinusoidal wave form and are introduced into wave form shaping circuit 202a, 202b, 202c, 202d to shape the sinusoidal waves into square wave. Square waves output signals from the wave form shaping circuits 202a and 202b are introduced into a first phase difference counter circuit 203a which counts the phase difference between the incident beam on the photoelectric elements 63 and 64. The results of the counting constitute data useful for obtaining the value of diopter in the manner described above. Similarly, square wave output signals from the wave form shaping circuits 202c and 202d are introduced into a second counter circuit 203b which counts the phase difference between the incident beams on the photoelectric elements 61 and 62. The results of the counting constitute data useful for obtaining the value of angle of astigmatic axis in the manner described above.

Results obtained by the first and second phase difference counter circuits 203a and 203b are put into first and second averaging means 302a and 302b, respectively. Each of the averaging means receives a plural number of data and makes an average of them. This averaging process serves to minimize possible error due to irregularity of data. The number of signals to be averaged by the process is the number of slit-like beams to be chopped and scanned by the rotary cylinder 33 at the time the beam rotating means 40, which is intermittently driven into rotation by a stepping motor 60, is stopped. The larger the number is, the higher the accuracy that can be obtained for measurement. The number is to be suitably selected considering the rotational frequency of the rotary cylinder 33 and beam rotating means 40 as well as the response characteristics of photoelectric elements 61 to 64.

Data of phase difference averaged by said first averaging means 302a are converted into values of diopter through conversion means 303. This conversion is carried out on the basis of conversion table or conversion formula and adequate correction are assured even when the relation between the phase difference signal and diopter value is non-linear. From one datum provided by said first averaging means 302a there is given one value of diopter through conversion means 303. This value is indicative of the scanning direction of the slit-like beam corresponding to the angular position of beam rotating means 40, that is, diopter on a meridian in this direction. Similarly, data of phase difference averaged by said second averaging means 302b constitute data for detecting the angle of astigmatic axis in the direction of scanning of the slit-like beam corresponding to the angular position of beam rotating means 40.

Meridional direction detection means 304 detects the angular position of beam rotating means 40, that is, the scanning direction of the slit-like beam directly from beam rotating means 40 or indirectly through the rotation of the stepping motor 60. Data of diopter values coming from conversion means 303 are sequentially stored in first memory means 305a. At the same time, data for detection of angle of the astigmatic axis are stored in second memory means 305b sequentially. After the data for detection of angle of astigmatic axis are stored throughout the continuous range of angle covering 180°, detection means for angle of astigmatic axis 306 reads out the stored data for detection of the angle of astigmatic axis to find an intermediate value between the maximum and minumum values of the data as described above. And said detection means 306 determines an angle corresponding to the found intermediate value as the angle of astigmatic axis. In this case, as previously mentioned, it is also possible to determine the angle of astigmatic axis by the angle at which the value of said data is zero. In this manner, in the range of one measurement covering 180° there are detected two values for the angle of astigmatic axis. Generally, these two values of angle are different by 90° from each other. Therefore, by adding 90° to or subtracting 90° from one detected angle of astigmatic axis, another angle of astigmatic axis can be automatically given. These two detection signals of angle of astigmatic axis obtained by said detection means 306 are supplied to detection means for diopter detection means 307. Said diopter detection means 307 selects values of diopter corresponding to the signals of angle from the diopter values previously stored sequentially in first memory means 305a. Thus, two diopter values, that is, the maximum value and the minimum value corresponding to the respective astigmatic axes can be obtained.

When the eye to be examined has no astigmatism, the two output signals from the photoelectric elements 61 and 62 have nearly the same phase. Therefore, in this case, data for detection of angle of astigmatic axis are all zero and no detection is made as to the angle of astigmatic axis. Thereby, diopter detection means 307 determines a diopter value within the measuring range covering 180° or the mean value of the measuring range to be the spherical diopter of the eye. The values of diopter detected in this manner are displayed in a predetermined form of display by means of display means 308.

To further improve the accuracy and stability of measurement there may be provided additionally blinking detection means 309 in the above described signal processing system. Such blinking detection means detects distortion of data due to blinking of the eye and may be provided, for example, in parallel with conversion means 303. When any distortion of data is detected by said blinking detection means, operation of conversion means 303 is stopped. A certain time after the interruption and when absence of distortion is confirmed, the operation of said conversion means is restarted. Provision of such blinking detection means serves to eliminate not only the noise caused by blinking of the eye but also various noises caused by some other factors.

Moreover, a further improvement of measurement accuracy can be attained by introducing into said blinking detection means the signals from four-divided photoelectric element 80 arranged on the optical axis of the light receiving member 37 to detect any possible misalignment of the eye with the eye-refractometer device. Also, a fifth photoelectric element may be provided around the rotary cylinder 33 or at other suitable position to take up a standing stray light component. By incorporating the stray light component, as an opposite phase component, into the output signal of the photoelectric element, a substantial reduction of noise component can be attained.

As shown in FIG. 13, all the steps of processing extending from first and second averaging means 302a and 302b to astigmatism detection means 306 and diopter detection means 307 may be controlled by a computer 300. By doing so, processing can be carried out at a very high speed and with high accuracy. Further, if the computer control is extended to the steps of conversion of values displayed by display means 308 and data output, then a full automatic eye-refractometer device can be provided. Also, the above embodiment may be modified in such manner that data of diopter value and of angle of astigmatic axis detected for every meridian can be recorded sequentially as given by conversion means and the examiner can read out from the recorded data the maximum and minimum diopters and the axis of astigmatism of the eye to be examined.

While in the above embodiment, beam rotating means 40 has been described and shown to be intermittently driven into rotation by a step motor 60, it should be understood that the present invention is never limited to the embodiment only. Said beam rotating means may be driven into rotation continuously and at a uniform speed within the scope of the invention. In this case, strictly speaking, the phase difference outputs coming from first and second phase difference detection means 203a and 203b will correspond to different meridional directions. However, it will be understood that data of phase difference for all of the meridional directions can be obtained also in this case when one considers the mean values given by first and second averaging means 302a and 302b as phase difference in the meridional direction corresponding to the center angle in a small range of rotational movement of beam rotating means 40 during the time of plural number of phase signals being issued from phase difference detection means 203a and 203b, that is, during the time of plural number of beams being chopped by the rotary cylinder 33.

The arrangement of eye-refractometer device according to the invention described above has many advantages over those of the prior art.

The eye-refractometer device of the invention contains only two moving structural members, that is, the rotary cylinder and beam rotating means and there is no need for using servo mechanism. Therefore, it is simple in structure and small in the overall size. For the above mentioned rotating members reciprocation is not required. Motion required therefor is only rotation in unidirection. This is very advantageous for speed-up of measurement. The speed of chopping of slit-like beam by the rotary cylinder can be increased up to the limit of response speed of photoelectric elements and therefore a larger amount of data can be taken in a certain given time.

Since separate photoelectric elements are used for detection of astigmatic axis and for detection of diopter in the eye-refractometer device according to the invention, the detection is scarcely affected by control of the eye to be examined. Use of a mean value of the maximum and minimum phase difference signals have an effect to minimize the influence of noise signals on the measurement and therefore a high accuracy of measurement can be assured. The eye-refractometer device is remarkably improved in accuracy although the measurement always involves unstable factors such as fine movement from fixation of the eye to be examined.

On the other hand, in the conventional measuring device of such type, the factor of noise component lies in that stray light is created chiefly by the movement of the optical member forming the measuring optical system, whereas in the construction of the present invention, only the rotary cylinder 33 and the light beam rotating means 40 are steadily rotated for the measurement and these effect no irregular movement, so that there is no danger of creating stray light to produce a great noise component. Also, the optical system is always fixed and therefore, the reflected light from the cornea of the eye to be examined which provides the greatest impediment in the measurement lies always at a predetermined position between the two light-receiving elements, thus enabling the flare from the cornea to be sufficiently removed.

As has hitherto been described, the present invention can not only achieve its intended purpose but also has various advantages and thus, provides an excellent eye-refractometer device.

We claim:

1. In an eye-refractometer device having a beam splitter; a projection optical system disposed in one optical path of said beam splitter to project a beam of light into the pupil of an eye to be examined therethrough and to effect scanning linearly thereof; a condensing optical system including a condenser lens fixedly provided in the other optical path of said beam splitter, a diaphragm member fixedly provided behind said condenser lens and a light receiving member fixedly provided further behind said diaphragm member at a conjugate point with the cornea of said eye relative to said condenser lens, said condensing optical system being disposed to condense the reflected light from the fundus of said eye on said light receiving member through said beam splitter; beam rotating member disposed at the eye side of said beam splitter to rotate the beam about the center of the optical path as its rotational axis; and a signal processing system for processing the signals coming from said light receiving member, the improvement wherein said light receiving member has a pair of photoelectric elements for detection of astigmatic axis and a pair of photoelectric elements for detection of diopter provided on the light receiving surface of said member apart from the optical axis of said condenser lens, said pair of astigmatic axis detection photoelectric elements being positioned on a straight line normal to the scanning direction of the beam projected through said projection optical system whereas said pair of diopter detection photoelectric elements being positioned on a line extending in said scanning direction, said signal processing system including first and second phase difference detection means for detecting the phase difference between the output signals from said pair of astigmatic axis detection photoelectric elements and the phase difference between the output signals between said pair of diopter detection photoelectric elements, respectively.

2. An eye-refractometer device according to claim 1, wherein said pair of astigmatic axis detection photoelectric elements is symmetrically disposed relative to the optical axis of said condenser lens and said pair of diopter detection photoelectric elements is symmetrically disposed relative to the optical axis of said condenser lens.

3. An eye-refractometer device according to claim 2, wherein said signal processing system further includes first and second averaging means for producing a signal of means value of signals from said first phase difference detection means and a signal of mean value of signals from said second phase difference detection means, respectively.

4. An eye-refractometer device according to claim 3, said beam projected through said projection optical system is a slit-like beam having a rectilinear cross section, said slit-like beam is scanned in a direction normal to the longitudinal direction of said slit-like beam and said diaphragm member has a slit-like opening extending in parallel with the longitudinal direction of said slit-like means.

5. An eye-refractometer apparatus comprising:
(a) a beam splitter,
(b) a projection optical system disposed in one optical path of said beam splitter, said projection optical system including a projection means for projecting a slit-like light beam having a rectilinear cross-section into the pupil of an eye to be examined and scanning means for linearly scanning the light beam in a direction normal to the longitudinal direction of said slit-like light beam in the pupil of the eye,
(c) a condensing optical system disposed in the other optical path of said beam splitter to condense the reflected light beam from the fundus of said eye, said condensing optical system including a condenser lens fixedly provided in said other optical path of said beam splitter, a diaphragm member fixedly provided behind said condenser lens and a light receiving member fixedly provided behind said diaphragm member at a conjugate position with the cornea of said eye with respect to said condenser lens,
said light receiving member having a first pair of photoelectric elements for detection of astigmatic axis and a second pair of photoelectric elements for detection of diopter provided on the light receiving surface of said member, photoelectric elements of said first pair disposed apart from each other on a straight line normal to the scanning direction of the slit-like light beam projected through said projection optical system whereas photoelectric elements of said second pair disposed apart from each other on a straight line parallel to the scanning direction of the slit-like light beam projected through said projection optical system,
(d) a beam rotating member disposed at the eye side of said beam splitter to rotate the light beam about the center of the optical path as its rotational axis, and
(e) a signal processing system including first phase difference detection means for detecting the phase difference between the output signals from said first pair of photoelectric elements and second phase difference detection means for detecting the phase difference between the output signals from said second pair of photoelectric elements.

6. An eye-refractometer apparatus according to claim 5, wherein said first pair of astigmatic axis detection photoelectric elements forms symmetrical disposition with respect to the optical axis of said condenser lens and also said second pair of diopter detection photoelectric elements forms symmetrical disposition with respect to the optical axis of said condenser lens.

7. An eye-refractometer apparatus according to claim 6, wherein said light receiving member further has a quadrant photocell for receiving reflected light from the cornea of the eye disposed on the optical axis of said condenser lens.

8. An eye-refractometer apparatus according to claim 7, further comprising another beam splitter disposed on that side of said beam rotating means which is adjacent to said eye, and a fixation optical system for directing a target light to the eye through said other beam splitter.

* * * * *